(12) United States Patent
Ueda et al.

(10) Patent No.: US 11,642,830 B2
(45) Date of Patent: May 9, 2023

(54) CONTAINER STERILIZATION METHOD AND CONTAINER STERILIZATION SYSTEM

(71) Applicant: MITSUBISHI HEAVY INDUSTRIES MACHINERY SYSTEMS, LTD., Kobe (JP)

(72) Inventors: Atsushi Ueda, Hyogo (JP); Kohichi Aoki, Hyogo (JP); Daisuke Tanaka, Tokyo (JP); Yasue Takeuchi, Tokyo (JP); Kohichi Tamura, Osaka (JP); Takashi Minamihonoki, Osaka (JP)

(73) Assignee: MITSUBISHI HEAVY INDUSTRIES MACHINERY SYSTEMS, LTD., Hyogo (JP)

( * ) Notice: Subject to any disclaimer, the term of this patent is extended or adjusted under 35 U.S.C. 154(b) by 352 days.

(21) Appl. No.: 17/060,955

(22) Filed: Oct. 1, 2020

(65) Prior Publication Data

US 2021/0031432 A1 Feb. 4, 2021

Related U.S. Application Data

(62) Division of application No. 15/532,497, filed as application No. PCT/JP2015/004009 on Aug. 10, 2015, now Pat. No. 10,857,719.

(30) Foreign Application Priority Data

Dec. 2, 2014 (JP) .............................. JP2014-244055

(51) Int. Cl.
*B29C 49/46* (2006.01)
*A61L 2/20* (2006.01)
(Continued)

(52) U.S. Cl.
CPC ................ *B29C 49/46* (2013.01); *A61L 2/20* (2013.01); *B65B 55/027* (2013.01); *B65B 55/04* (2013.01);
(Continued)

(58) Field of Classification Search
CPC .......... B29C 49/46; A61L 2/202; B65B 55/10
See application file for complete search history.

(56) References Cited

U.S. PATENT DOCUMENTS 4,680,163 A 7/1987 Blidschun et al.
5,855,856 A 1/1999 Karlson
(Continued)

FOREIGN PATENT DOCUMENTS

EP 0436042 A1 7/1991
JP S60236654 A 11/1985
(Continued)

OTHER PUBLICATIONS

EP Office Action for 15 866 207.2 dated Nov. 4, 2021, 7 pp.
(Continued)

*Primary Examiner* — Kevin Joyner
(74) *Attorney, Agent, or Firm* — Kanesaka Berner and Partners LLP (57) ABSTRACT

Provided is a novel container sterilization method in which no liquid agent is used. A container sterilization method is a method of performing sterilization by supplying a sterilization component to a container that is continuously conveyed along a predetermined conveyance path, the container sterilization method including supplying a humid ozone gas to a sterilization area, the humid ozone gas being an ozone gas that has humidity, the sterilization area being partitioned by a sterilization chamber that contains the conveyance path. The humidity of the humid ozone gas to be supplied to the sterilization region is regulated, depending on a temperature of the containers to be conveyed to the sterilization region.

5 Claims, 7 Drawing Sheets

(51) Int. Cl.
  *B65B 55/10* (2006.01)
  *B65B 55/04* (2006.01)
  *B65B 55/02* (2006.01)
  *B65B 3/02* (2006.01)
  *B67C 7/00* (2006.01)

(52) U.S. Cl.
  CPC .............. *B65B 55/10* (2013.01); *B65B 3/022* (2013.01); *B67C 7/00* (2013.01)

(56) References Cited

U.S. PATENT DOCUMENTS

| | | | |
|---|---|---|---|
| 7,993,603 | B2 | 8/2011 | Amedeo et al. |
| 2006/0067856 | A1 | 3/2006 | Martensson et al. |
| 2007/0237671 | A1 | 10/2007 | Yuan et al. |
| 2011/0076192 | A1 | 3/2011 | Robitaille et al. |
| 2016/0001488 | A1 | 1/2016 | Cluesserath |
| 2016/0009433 | A1 | 1/2016 | Tanaka et al. |

FOREIGN PATENT DOCUMENTS

| | | |
|---|---|---|
| JP | H11105834 A | 4/1999 |
| JP | 2003220121 A | 8/2003 |
| JP | 2004106920 A | 4/2004 |
| JP | 2005350071 A | 12/2005 |
| JP | 2008207842 A | 9/2008 |
| JP | 2013172986 A | 9/2013 |
| JP | 2014080207 A | 5/2014 |
| JP | 2014181039 A | 9/2014 |
| WO | 2014127903 A1 | 8/2014 |

OTHER PUBLICATIONS

Muranyi et al. "Influence of relative gas humidity on the inactivation efficiency of a low temperature gas plasma" Journal of Applied Microbiology, 2008, pp. 1659-1666; 8pp.

Rutala et al. "Guideline for Disinfection and Sterilization in Healthcare Facilities, 2008" 2008, pp. 1-158; 158pp.

Extended European Search Report of European Application No. 15866207.2 dated Sep. 4, 2018; 8pp.

International Search Report and Written Opinion of International Application No. PCT/JP2015/004009 dated Nov. 2, 2015; 15pp.

CONTAINER STERILIZATION METHOD AND CONTAINER STERILIZATION SYSTEM

RELATED APPLICATIONS

The present application is a divisional of U.S. application Ser. No. 15/532,497 filed Jun. 1, 2017, which is a National Phase of International Application Number PCT/JP2015/004009 filed Aug. 10, 2015 which claims priority to Japanese Application Number 2014-244055 filed Dec. 2, 2014, the disclosures of which are hereby incorporated by reference herein in their entirety.

TECHNICAL FIELD

The present invention relates to a sterilization method for a container that is filled with a liquid such as drinking water, for example.

BACKGROUND ART

As a system that fills a liquid such as drinking water into a container such as a PET (Polyethylene terephthalate) bottle, a glass bottle or a bottle can, a rotary filling apparatus is used. The rotary filling apparatus includes a plurality of filling valves at an outer circumferential portion of a rotating body. The filling into the container from the filling valve is performed while the container is conveyed in the circumferential direction by roughly one rotation of the rotating body. Then, after the filling into the container is finished, a cap is attached to the container by a capper or a capping machine.

Among the above containers, the PET bottle is molded by blowing air into a test-tube-like precursor called a preform. For the molding, a biaxial stretch blow molding method is mainly used. The biaxial stretch blow molding method is a molding method in which a heated preform is inserted into a mold and thereafter is inflated in the circumferential direction by blowing a pressurized air while the preform is stretched in the vertical direction by a rod called a stretching rod. Incidentally, as the molding method for the preform, two types: an injection molding method and a PCM (Preform Compression Molding) molding method are known.

As beverage filling systems intended for the PET bottle, there are a mode in which a molding apparatus for the PET bottle is included on the upstream side and the molded PET bottle is supplied to the filling apparatus and a mode in which an already molded PET bottle is prepared and is supplied to the filling apparatus.

By the way, in the case where a liquid such as a drinking water is filled, it is necessary to prevent the container from being contaminated by bacteria, with no limit. Accordingly, there is employed a so-called aseptic filling technique in which a sequence of processes such as container sterilization, rinse, cap sterilization, liquid filling and cap attachment are performed in a clean room. In the case of the beverage filling system including the molding apparatus for the PET bottle on the upstream side, it is sometimes required to sterilize the PET bottle molded by the molding apparatus, before supplying the PET bottle to the filling apparatus.

For the sterilization in the aseptic filling technique, an agent, for example, a peracetic acid type disinfectant composed of an aqueous solution containing peracetic acid (PAA) or hydrogen peroxide ($H_2O_2$) is used (for example, Patent Literatures 1, 2).

CITATION LIST

Patent Literature

Patent Literature 1: JP 2014-181039 A
Patent Literature 2: JP 2014-080207 A

SUMMARY OF INVENTION

Technical Problem

However, in the case where peracetic acid is used as a disinfectant, there is a problem in that bacteria resistant to peracetic acid are produced. As for hydrogen peroxide, there is no problem of resistant bacteria. However, in the case of being intended for the PET bottle, there is a problem in that hydrogen peroxide is absorbed in PET and remains in the container.

Hence, the present invention has an object to solve the problem and to provide a novel container sterilization method in which no liquid agent is used.

Solution to Problem

The inventors have studied the use of ozone ($O_3$) for container sterilization in a beverage filling system, and as a result, have found that it is possible to achieve a required sterilization power by supplying an ozone gas (hereinafter, referred to as a "humid ozone gas") having humidity to the container that is continuously conveyed.

A container sterilization method according to the present invention, which is based on the findings, is a method of performing sterilization by supplying a sterilization component to a plurality of containers that are continuously conveyed along a predetermined conveyance path, the container sterilization method including supplying a humid ozone gas to a sterilization region, the humid ozone gas being an ozone gas that has humidity, the sterilization region being partitioned by a chamber that contains the conveyance path.

In the sterilization method according to the present invention, it is preferable that the humid ozone gas to be supplied to the sterilization region have a higher temperature than the container to be conveyed to the sterilization region.

Thereby, the humid ozone gas is condensed on a surface of the container, so that a high sterilization efficiency can be secured.

In the sterilization method according to the present invention, it is preferable that the chamber have a higher temperature than the container to be conveyed to the sterilization region.

Thereby, the humid ozone gas is easily condensed on the container, instead of on the chamber.

In the sterilization method according to the present invention, it is preferable that the humidity of the humid ozone gas to be supplied to the sterilization region be regulated, depending on a temperature of the container to be conveyed to the sterilization region.

Thereby, it is possible to secure the condensation of the humid ozone gas on the surface of the container.

In the sterilization method according to the present invention, it is preferable that a temperature of the container to be supplied to the sterilization region be regulated, depending on the humidity of the humid ozone gas to be supplied to the sterilization region.

Thereby, similarly, it is possible to secure the condensation of the humid ozone gas on the surface of the container.

In the sterilization method according to the present invention, it is preferable that the humid ozone gas to be supplied to the sterilization region be generated by contact between an ozone gas having a lower humidity than the humid ozone gas and moisture.

Thereby, it is possible to generate the humid ozone gas having an arbitrary humidity.

In the sterilization method according to the present invention, when the humid ozone gas to be supplied to the sterilization region is introduced into an interior of the container, it is possible to sterilize an inner circumferential surface of the container.

In the sterilization method according to the present invention, when the humid ozone gas to be supplied to the sterilization region is supplied to a periphery of the container, the humid ozone gas can sterilize an outer circumferential surface of the container, and by depressurizing an interior of the container, the humid ozone gas can be sucked into the interior from the periphery and can sterilize an inner circumferential surface of the container.

Further, a container sterilization system according to the present invention includes: a conveyance path along which a plurality of containers are continuously conveyed; a sterilization region that is provided on the conveyance path, the sterilization region being partitioned by a chamber that contains the conveyance path; and a humid gas generation unit that generates a humid ozone gas, the humid ozone gas being supplied to the sterilization region as a sterilization component, the humid ozone gas being an ozone gas that has humidity.

In the sterilization system according to the present invention, it is preferable that the humid gas generation unit generate the humid ozone gas having a higher temperature than the container to be conveyed to the sterilization region.

In the sterilization system according to the present invention, it is preferable that the chamber have a higher temperature than the container to be conveyed to the sterilization region.

In the sterilization system according to the present invention, it is preferable that the humid gas generation unit generate the humid ozone gas by contact between an ozone gas having a lower humidity than the humid ozone gas and moisture. Here, the moisture includes both a liquid state and a gas state.

In the sterilization system according to the present invention, it is preferable that the humid gas generation unit generates the humid ozone gas while regulating the humidity of the humid ozone gas depending on a temperature of the container to be conveyed to the sterilization region.

In the sterilization system according to the present invention, it is preferable to include a temperature regulator that regulates a temperature of the container to be supplied to the sterilization region, depending on the humidity of the humid ozone gas to be supplied to the sterilization region.

In the sterilization system according to the present invention, it is preferable to include means for supplying the humid ozone gas to an interior of the container to be conveyed to the sterilization region, the means being inserted into the interior of the container.

In the sterilization system according to the present invention, it is preferable to include: depressurization means for depressurizing an interior of the container to be conveyed to the sterilization region; and means for supplying the humid ozone gas to a periphery of the container.

Advantageous Effects of Invention

According to the present invention, the humid ozone gas is used for the sterilization, and the ozone gas does not produce resistant bacteria. Further, in the case where the container is composed of, for example, PET, the ozone gas does not remain in the container. Moreover, according to the present invention, by providing the sterilization region partitioned by the chamber that contains the conveyance path, it is possible to prevent the leak of the ozone to the exterior. Furthermore, by using the humid ozone gas, it is possible to sufficiently obtain a sterilization efficiency required for a beverage container.

BRIEF DESCRIPTION OF DRAWINGS

FIG. 4A and FIG. 4B show a rotating table in the embodiment, in which

DESCRIPTION OF EMBODIMENTS

Hereinafter, the present invention will be described in detail, based on embodiments shown in the attached drawings.

Figure 1:
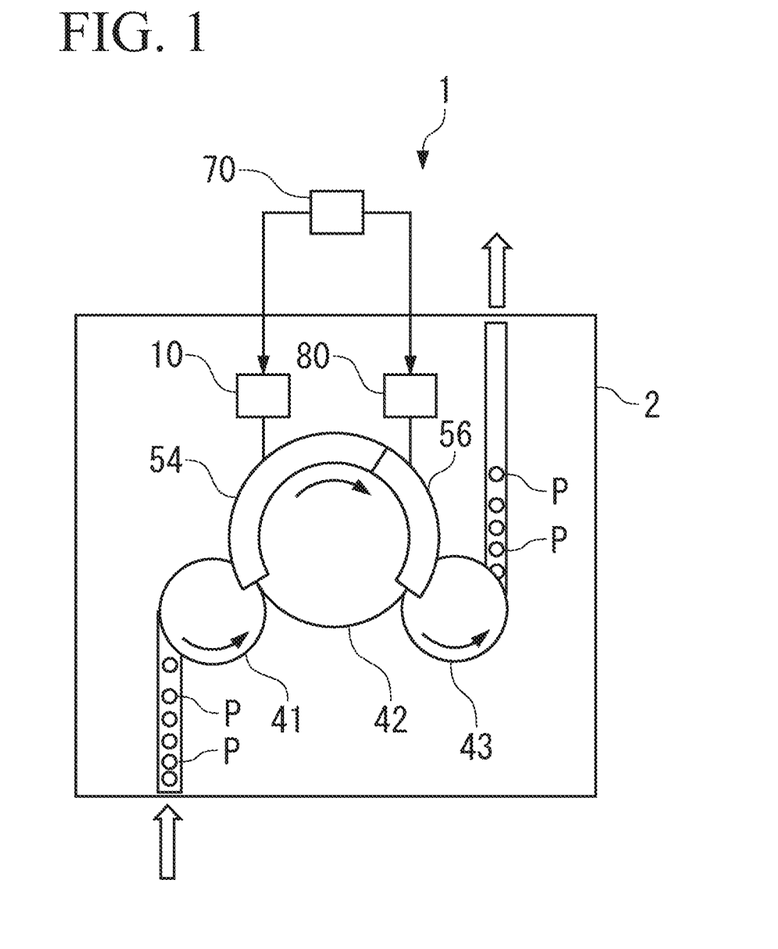
FIG. 1 is a plan view showing a schematic configuration of a container sterilization system in the embodiment.

As shown in FIG. 1, a beverage container sterilization system 1 according to the embodiment includes a humid gas generation unit 10 that generates a humid ozone gas, a sterilization unit 40 that sterilizes a beverage container P, by introducing the humid ozone gas generated by the humid gas generation unit 10 and supplying the humid ozone gas to the container P to be conveyed, and a control unit 70 that controls the operations of the humid gas generation unit 10 and the sterilization unit 40. The humid gas generation unit 10 and the sterilization unit 40 are provided in the interior of an aseptic room 2.

[Humid Gas Generation Unit 10]

Figure 2:
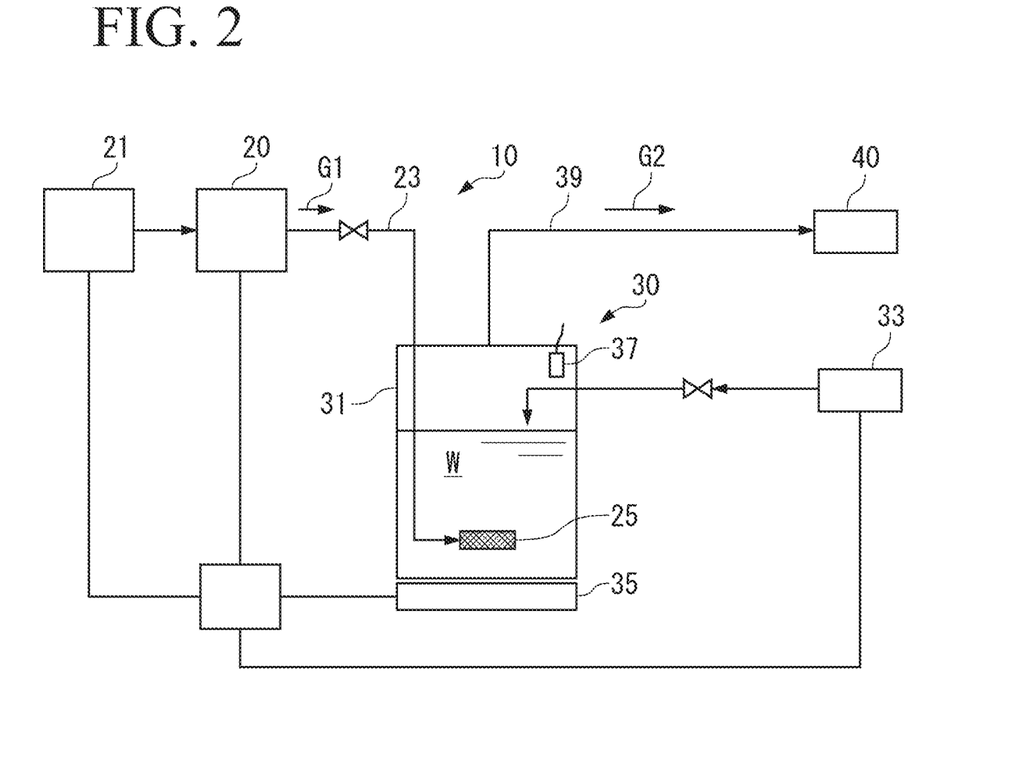
FIG. 2 is a diagram showing an exemplary configuration of a gas generation unit of the sterilization system in FIG. 1.

As shown in FIG. 2, the humid gas generation unit 10 includes an ozone generation apparatus 20 that generates dry-state ozone ($O_3$) and feeds the generated ozone to a humidification apparatus 30, and the humidification apparatus 30 that humidifies the fed dry-state ozone. The humid gas generation unit 10 generates a humid ozone gas G2 by a so-called bubbling technique. The ozone gas humidified by the humidification apparatus 30 is fed to a sterilization unit 40.

The ozone generation apparatus 20 generates a mixed gas G1 of ozone and oxygen, using an oxygen ($O_2$) gas to be supplied from a raw material supply source 21 as a raw material. The concentration of ozone in the mixed gas is, for example, about 5 to 15 vol %, and typically, 10 vol %. Here, the raw material is not limited to oxygen, and for example, a gas containing oxygen, for example, air may be used.

The ozone generation technique includes a silent discharge technique, an electrolysis technique, an ultraviolet lamp technique and the like. For the industrial use, the silent discharge technique is used, and, also in the embodiment, it is preferable to apply the silent electric discharge technique.

However, it is allowed to employ another technique. Here, the silent discharge is a discharge phenomenon that is observed when a dielectric is provided between parallel electrodes, oxygen gas is supplied to the interval and a high alternating-current voltage is applied between both electrodes. By the silent discharge, electrons e are released in the gas. Ozone is generated by a first step in which the electron e collides with a stable oxygen molecular $O_2$ so that the oxygen molecular $O_2$ dissociates into oxygen atoms O, and a second step in which a triple collision of the oxygen atom O, the oxygen molecule $O_2$ and a third substance M (for example, nitrogen molecule) occurs. The mixed gas contains the third substance M.

First step:

Second step:

The dry-state mixed gas G1 generated by the ozone generation apparatus 20 is supplied to the humidification apparatus 30 through a first pipe 23. To an end of the first pipe 23, a nozzle 25 composed of a porous material is attached. The nozzle 25 is immersed in water W that is stored in a water tank 31 of the humidification apparatus 30.

The humidification apparatus 30 includes the water tank 31 in which the mixed gas G1 comes in contact with the previously stored water W, a water supply source 33 that supplies the water W to the water tank 31, a heater 35 that heats the water stored in the water tank 31, a first temperature sensor 37 that measures the temperature of a space region that is in the interior of the water tank 31 and above the water W, and a second pipe 39 that supplies the generated humid ozone gas G2 to the sterilization unit 40. As is clear from the above description, the humid ozone gas G2 contains the third substance M other than $O_3$ (ozone), and has humidity.

The mixed ozone gas G1 discharged from the nozzle 25, which is immersed in the water W stored in the water tank 31, rises in the water W, as minute bubbles, and comes in contact with the water W in the course of the rise. Thereby, the mixed ozone gas G1 becomes the humid ozone gas G2, and the humid ozone gas G2 is released from the surface of the water W. The released humid ozone gas G2 passes through the void region of the water tank 31 and the second pipe 39 in order, and is supplied to the sterilization unit 40. Main component elements of the humid ozone gas G2 are oxygen ($O_2$), ozone ($O_3$) and water ($H_2O$).

The water W stored in the water tank 31 is heated to a range of 60 to 100° C., typically, to 80° C., by the heater 35. Therefore, the humid ozone gas G2 released from the surface of the water W is also controlled to a temperature nearly equal to the heating temperature of the water W, and is supplied to the sterilization unit 40.

It is preferable that the relative humidity RH of the humidity ozone gas G2 at the temperature of the container P to be conveyed to the sterilization unit 40 be in a range of 45 to 100%. This is because a sufficient sterilization power is obtained when the relative humidity RH of the humid ozone gas G2 is 45% or more, and conversely, the sterilization power deteriorates when the relative humidity RH of the humid ozone gas G2 exceeds 100%. More preferably, the relative humidity RH should be 80 to 100%, and further preferably, the relative humidity RH should be 95 to 100%.

The relative humidity RH herein is the relative humidity RH at the temperature of the container P to be conveyed to the sterilization unit 40, and is different from the relative humidity at the time when the humid ozone gas G2 is generated by the humidification apparatus 30. In other words, the relative humidity RH of the humid ozone gas G2 to be generated by the humidification apparatus 30 should be regulated, in consideration of the temperature of the container P that is the sterilization object and to which the humid ozone gas G2 is supplied. In this respect, a further description will be made later.

[Sterilization Unit 40]

The sterilization unit 40 performs the sterilization by making the humid ozone gas G2 supplied from the humid gas generation unit 10 act on the inner circumferential surface and outer circumferential surface of the container P to be continuously conveyed from the upstream process, and transfers the container P for which the sterilization is completed, to the downstream process.

As shown in FIG. 1, the sterilization unit 40 includes a first rotating table 41 that receives the container P conveyed from the upstream process and that holds and conveys the container P, a second rotating table 42 that receives the container P conveyed by the first rotating table 41 and that holds and conveys the container P, and a third rotating table 43 that receives the container P conveyed by the second rotating table 42 and that holds and conveys the container P. The respective rotating tables 41 to 43 are configured to be rotatable by electric motors, which are omitted in the figure.

The respective rotating tables 41 to 43 include elevating grippers 46 (see FIG. 4A) each of which can move the container P up and down while holding the neck of the container P. The plurality of elevating grippers 46 are provided so as to be at equal intervals in the circumferential directions of the respective rotating tables 41 to 43 and to penetrate the rotating tables 41 to 43.

Figure 4A:
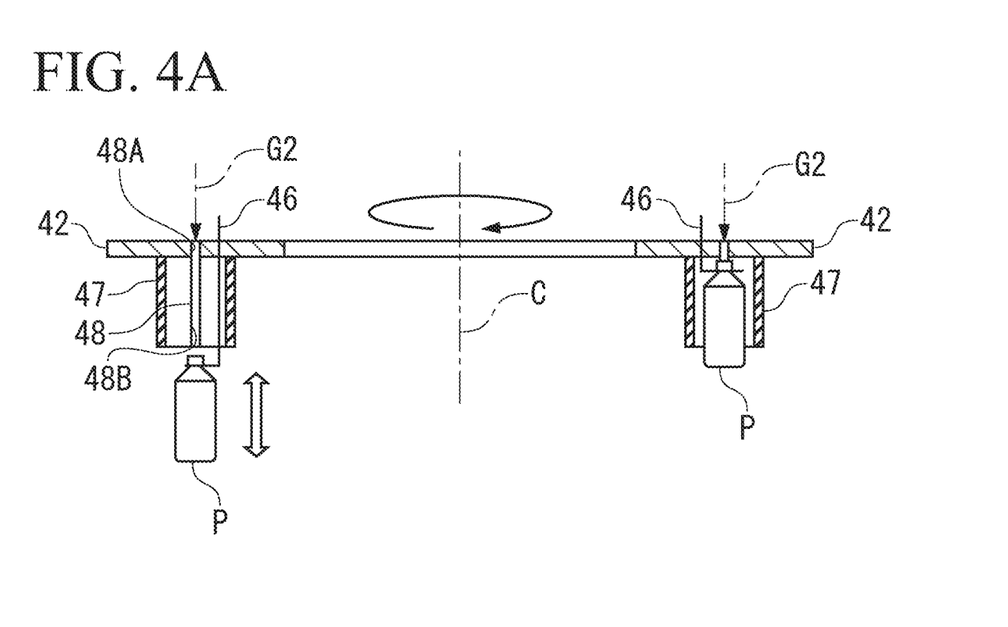
FIG. 4A shows a mode of blowing a humid ozone gas and FIG. 4B shows a mode of sucking the humid ozone gas.

As shown in FIG. 4A, the second rotating table 42 includes shield cylinders 47 and gas supply nozzles 48, corresponding to the respective elevating grippers 46.

The shield cylinder 47 makes the humid ozone gas G2 stay between the container P to be sterilized and the shield cylinder 47, while covering the periphery of the container P, and thereby, accelerates the sterilization of the outer circumferential surface of the container P.

The shield cylinder 47 has a circular cylinder shape, and one end portion in the axis direction is fixed to the lower surface of the second rotating table 42 such that the shield cylinder 47 surrounds the elevating gripper 46. As shown in the left side of FIG. 4A, when the elevating gripper 46 surrounded by the shield cylinder 47 moves to the lowermost position, the holding portion is exposed from the end (lower end) of the shield cylinder 47. Further, as shown in the right side of FIG. 4A, when the elevating gripper 46 moves to the uppermost position, the holding portion reaches the vicinity of the lower surface of the second rotating table 42, and most of the outer circumferential surface of the container P is covered with the shield cylinder 47.

The gas supply nozzle 48, to which the humid ozone gas G2 generated by the humid gas generation unit 10 is supplied, discharges the humid ozone gas G2 toward the container P. The gas supply nozzle 48 and the held container P are coaxially arranged.

The gas supply nozzle 48 is provided so as to penetrate the second rotating table 42 in the thickness direction, and an inlet port 48A for the humid ozone gas G2 is opened on the upper surface of the second rotating table 42. The length of the gas supply nozzle 48 is set such that a discharge port 48B provided at an end portion opposite to the inlet port 48A reaches the vicinity of the bottom of the container P when the container P moves to the uppermost position. In the embodiment, the gas supply nozzle 48, which is provided in the interior of the shield cylinder 47, has a length equivalent to that of the shield cylinder 47.

The gas supply nozzle 48, in a rinse area 60, functions as a nozzle for supplying the air for rinse.

The elevating gripper 46, the shield cylinder 47 and the gas supply nozzle 48 move so as to revolve around a rotation axis C, in connection with the rotation of the second rotating table 42.

The first and third rotating tables 41, 43 have a simple structure of performing only the rotation conveyance while holding the container P.

Next, as shown in FIG. 1, FIG. 3 and FIGS. 5A to 5F, the sterilization unit 40 includes a sterilization area 50 and the rinse area 60 on the second rotating table 42.

[Sterilization Area 50]

As shown in FIG. 3 and FIGS. 5A to 5F, the sterilization area 50 includes a sterilization chamber 51 and a rinse chamber 61 that are provided so as to contact with the lower surface of the second rotating table 42, and gas retention chambers 54, 56 that are provided so as to contact with the upper surface of the second rotating table 42.

The sterilization chamber 51, whose transverse section has a C-shape, is arranged such that the opening side is oriented upward and contacts with the lower surface of the second rotating table 42. The sterilization chamber 51 contains, in the interior, the elevating gripper 46, the shield cylinder 47 and the gas supply nozzle 48 that are provided on the second rotating table 42. The container P held by the elevating gripper 46 moves from the upstream side to the downstream side in the interior of the sterilization chamber 51, in connection with the rotation of the second rotating table 42. In the course of the movement, a predetermined sterilization treatment is performed for the container P. The sterilization chamber 51 has an arc shape in planar view (see FIG. 1). The same goes for the gas retention chamber 56.

Unlike the rotation motion of the second rotating table 42, the position of the sterilization chamber 51 is fixed. Accordingly, the contact portion between the sterilization chamber 51 and the second rotating table 42 slides in connection with the rotation motion of the second rotating table 42.

Figure 3:
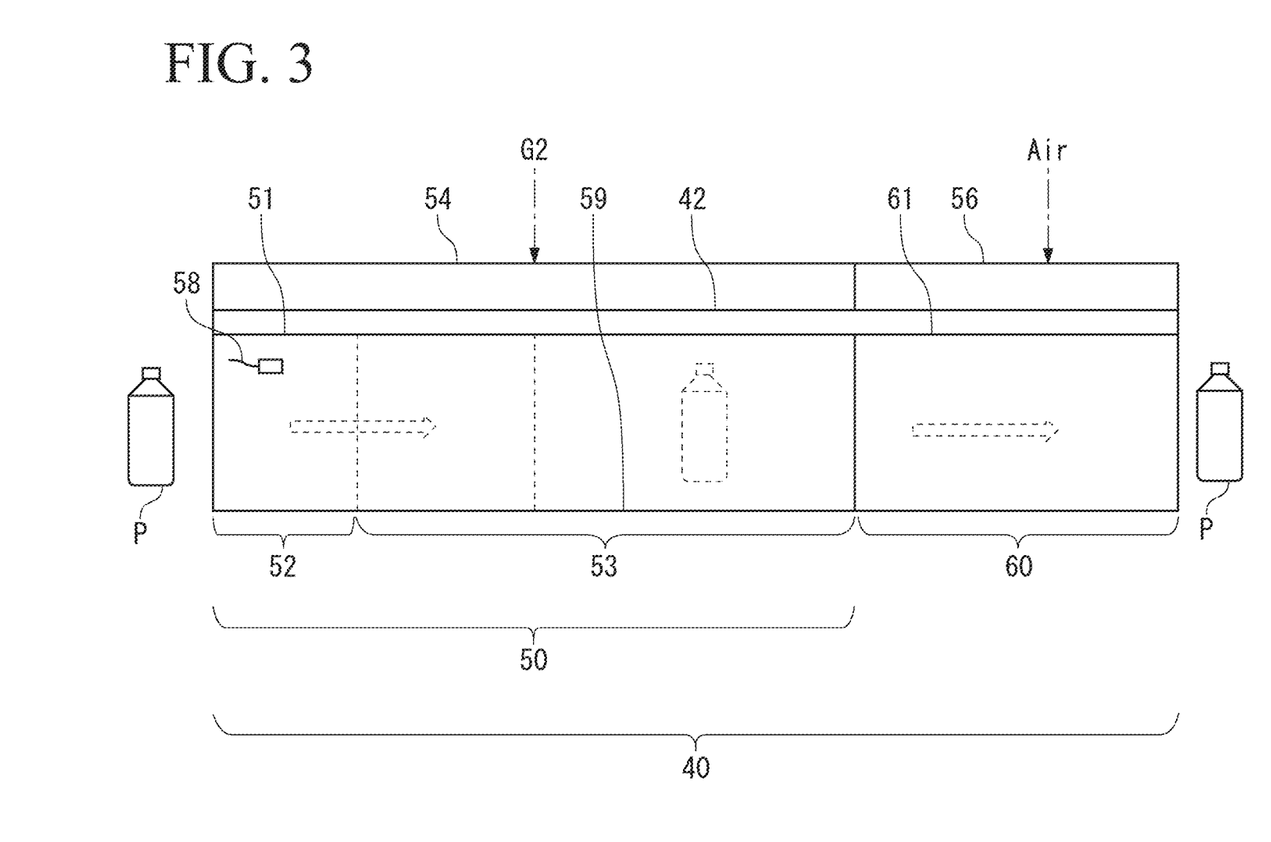
FIG. 3 is a linearly expanded diagram showing a sterilization region in the embodiment.

As shown in FIG. 3, the sterilization chamber 51 includes an emission region 52 and a sterilization region 53.

The emission region 52 is a region for supplying the humid ozone gas G2 from the gas supply nozzle 48 to the interior and forcibly emitting the gas containing the humid ozone gas G2 in the interior. The forcibly emitted gas is stored in a predetermined emission gas facility, and thereby, the humid ozone gas G2 is prevented from leaking to an unintended place. For achieving this purpose, in the emission region 52, as shown in FIGS. 5A and 5B, the sterilization chamber 51 is provided with an exhaust pipe 55.

Figure 5A:
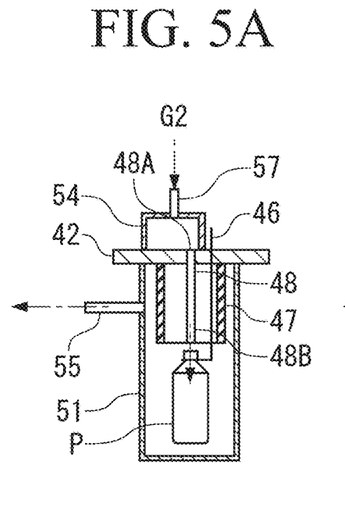
FIG. 5A to FIG. 5F are diagrams showing a procedure for sterilizing a container P in the blow mode.
Figure 5B:
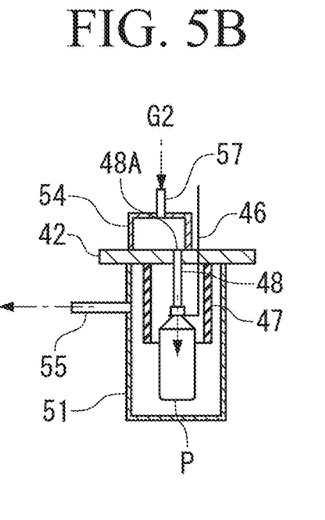
Figure 5C:
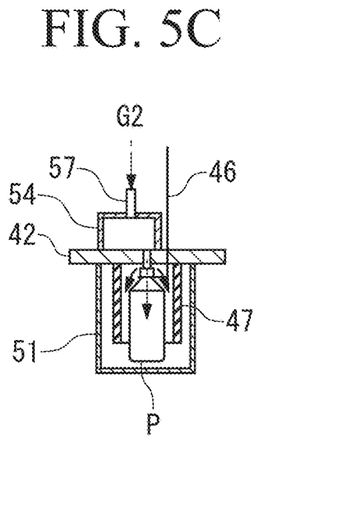

The sterilization region 53 is a region for sterilizing mainly the inner circumferential surface of the container P, and as shown in FIG. 5C, the container P is conveyed while the gas supply nozzle 48 is inserted into the interior. Thereafter, the container P is conveyed to the subsequent rinse area 60 while being held by the elevating gripper 46 of the second rotating table 42.

As shown in FIGS. 5A to 5C, the height of the sterilization chamber 51 can vary along the conveyance direction of the container P, depending on the degree of the elevation of the container P by the elevating gripper 46. That is, at the time of the transfer of the container P, it is necessary to elevate the container P for moving the container P to the outside of the end of the shield cylinder 47, and by that quantity, it is necessary to increase the height of the sterilization chamber 51. However, in the other regions, the height is decreased for avoiding the humid ozone gas G2 from being needlessly supplied. In FIG. 3, the height of the sterilization chamber 51 is illustrated as a constant height. The same goes for the rinse chamber 61.

Next, as shown in FIG. 3 and FIGS. 5A to 5C, the gas retention chamber 54, whose transverse section has a C-shape, is arranged such that the opening side is oriented downward and contacts with the upper surface of the second rotating table 42. The gas retention chamber 54 is provided at a position where the gas retention chamber 54 does not interfere with the elevating gripper 46 and covers the inlet port 48A of the gas supply nozzle 48 that is opened on the upper surface of the second rotating table 42.

Unlike the sterilization chamber 51, the region of the gas retention chamber 54 is not sectioned, and the gas retention chamber 54 has a uniform opening area from the upstream side to the downstream side in the conveyance direction.

At a plurality of spots in the conveyance direction, the gas retention chamber 54 is provided with introduction pipes 57 for introducing the humid ozone gas G2 to the interior, and the respective introduction pipes 57 are connected with the second pipe 39 of the humidification apparatus 30.

Unlike the rotation motion of the second rotating table 42, the position of the gas retention chamber 54 is also fixed. Accordingly, the contact portion between the gas retention chamber 54 and the second rotating table 42 slides in connection with the rotation motion of the second rotating table.

As shown in FIG. 3, in the emission region 52, which is positioned at the most upstream side of the sterilization chamber 51, a second temperature sensor 58 that measures the temperature of the container P to be conveyed is provided. The temperature of the container P measured by the second temperature sensor 58 is sent to the control unit 70, and is used for the control of the relative humidity RH of the humid ozone gas G2 generated in the humid gas generation unit 10 and the management of the temperature of the sterilization chamber 51.

As shown in FIG. 3, a sheet-shaped heater 59 is provided in the sterilization chamber 51, and by the control unit 10, the heater 59 is controlled to a higher temperature than that of the container P to be conveyed, based on the measurement result of the second temperature sensor 58.

[Rinse Area 60]

Next, as shown in FIG. 3 and FIGS. 5D to 5F, the rinse area 60 includes the rinse chamber 61 that is provided so as to contact with the lower surface of the second rotating table 42, and the gas supply nozzle 48 that penetrates the second rotating table 42.

Figures 5D, 5E:
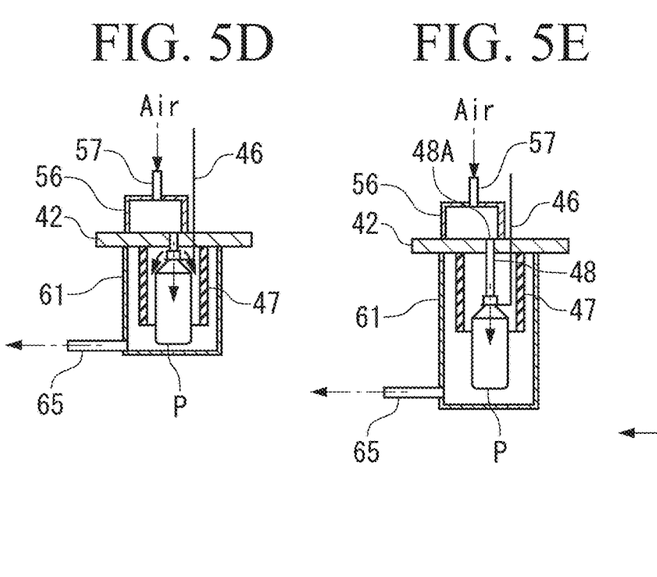
Figure 5F:
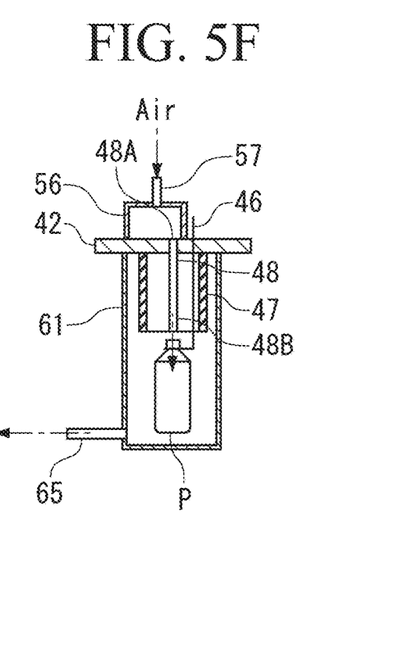

The rinse chamber 61, whose transverse section has a C-shape, is arranged such that the opening side is oriented upward and contacts with the lower surface of the second rotating table 42. The container P held by the elevating gripper 46 moves from the upstream side to the downstream side in the interior of the rinse chamber 61, in connection with the rotation of the second rotating table 42. In the course of the movement, a predetermined rinse treatment is performed for the container P.

Unlike the rotation motion of the second rotating table 42, the position of the rinse chamber 61 is fixed. Accordingly, the contact portion between the rinse chamber 61 and the second rotating table 42 also slides in connection with the rotation motion of the second rotating table 42.

As shown in FIGS. 5D to 5F, the rinse chamber 61 is provided with an exhaust pipe 65, for forcibly emitting the humid ozone gas G2 supplied in the sterilization area 50 and the air blown for rinse. The forcibly emitted gas is stored in a predetermined emission gas facility, and thereby, the humid ozone gas G2 is prevented from leaking to an unintended place.

Next, as shown in FIG. 3 and FIGS. 5D to 5F, the gas retention chamber 56, whose transverse section has a C-shape, has the same configuration as the gas retention chamber 54, except that the gas retention chamber 56 is separated from the gas retention chamber 54 and the introduction pipe 57 is connected with a supply source 80 (see FIG. 1) of the air for rinse.

[Control Unit 70]

The control unit 70 controls the operations of the humid gas generation unit 10 and the sterilization unit 40 (see FIG. 1). Particularly, the control unit 70 in the embodiment controls the relative humidity RH of the humid ozone gas G2 to be generated in the humid gas generation unit 10, and controls the temperature of the heater 59 such that the temperature of the sterilization chamber 51 is maintained at a higher temperature than that of the container P to be conveyed.

The sterilization efficiency of the humid ozone gas G2 depends on the relative humidity RH with respect to the sterilization object body. Accordingly, the second temperature sensor 58 measures the temperature of the container P that is the sterilization object, and the control unit 70 acquires the measurement result and evaluates a relative humidity RH at which a high sterilization efficiency is obtained at the current time. The control unit 70 evaluates operating conditions of the ozone generation apparatus 20 and the humidification apparatus 30 that are necessary to obtain the relative humidity RH, and instructs each to operate the operating condition. For increasing the relative humidity RH, there may be employed a method of decreasing the diameter of the bubble of the mixed gas G1 blown into the water W, a method of increasing the time during which the bubble of the blown mixed gas G1 contacts with the water W, a method of increasing the heating temperature of the water W by the heater 35, a method of increasing the capacity of the water tank 31 and increasing the contact area of the mixed gas G1 with the water W, or a method of increasing the size of the water tank 31 and increasing the contact area with the water W.

For effectively consuming the humid ozone gas G2 supplied to the sterilization chamber 51 for the sterilization of the container P, it is necessary to avoid the humid ozone gas G2 from condensing and attaching to the sterilization chamber 51. Hence, in the embodiment, the control unit 70 acquires the temperature of the container P measured by the second temperature sensor 58, and based on the measurement result, the control unit 70 controls the temperature of the heater 59 such that the sterilization chamber 51 is maintained at a higher temperature than that of the container P to be conveyed.

[Sterilization Treatment Procedure]

In the following, a procedure of the sterilization treatment of the container P using the sterilization system 1 will be described.

The container P continuously conveyed from the upstream side is transferred to the second rotating table 42 through the first rotating table 41. The second temperature sensor 58 measures the temperature of the container P transferred to the second rotating table 42, and the control unit 70 acquires the result.

The container P transferred to the second rotating table 42 is conveyed to the emission region 52 of the sterilization chamber 51, in connection with the rotation motion of the second rotating table 42. As shown in FIG. 5A, the container P conveyed to the emission region 52 is positioned below the shield cylinder 47. However, as shown in FIG. 5B, the elevating gripper 46 rises with the progression of the conveyance, and thereby, the container P enters the interior of the shield cylinder 47. In the emission region 52, the humid ozone gas G2 having passed through the introduction pipe 57 and the gas retention chamber 54 is discharged from the gas supply nozzle 48 toward to the container P. Meanwhile, the gas in the interior of the sterilization chamber 51 is emitted to the exterior through the exhaust pipe 55.

After passing through the emission region 52, the container P reaches the sterilization region 53.

In the sterilization region 53, as shown in FIG. 5C, the container P passes through a region where the opening area of the transverse section of the sterilization chamber 51 is smallest.

In the sterilization region 53, since the gas supply nozzle 48 is inserted into the interior of the container P, the humid ozone gas G2 discharged from the gas supply nozzle 48 acts on the inner circumferential surface of the container P, to perform the sterilization treatment. Some of the humid ozone gas G2 overflows from the container P, floats in the interspace between the container P and the shield cylinder 47, and therewith, acts on the outer circumferential surface of the container P, to perform the sterilization treatment of the outer circumferential surface of the container P. For promoting the condensation of the humid ozone gas G2 on the container P, it is desirable that the humid ozone gas G2 be higher in humidity than the container P. Here, it is allowable to provide a nozzle for supplying the humid ozone gas directly to the outer circumferential surface of the container P.

When the humid ozone gas G2 acts on the inner circumferential surface and outer circumferential surface of the container P, the condensation based on the humid ozone gas G2 may be generated on the inner circumferential surface and the outer circumferential surface. From a standpoint of the sterilization efficiency, the condensation dispersed into minute water droplets is preferable. However, excessive condensation is not preferable, and for example, it is not preferable that the inner circumferential surface or the outer circumferential surface gets so wet that the condensation water forms a uniform continuous film. The preferable action condition of the humid ozone gas G2 on the container P can be evaluated experimentally.

The sterilization chamber 51 is heated by the heater 59, based on the control by the control unit 70, and therefore, the supplied humid ozone gas G2 is not condensed on the sterilization chamber 51, and is effectively consumed for the sterilization treatment of the container P.

After passing through the sterilization region 53, the container P reaches the rinse area 60. As shown in FIGS. 5D to 5F, in the rinse area 60, the container P is conveyed in the interior of the rinse chamber 61 while being held by the elevating gripper 46.

In the rinse chamber 61, the air for rinse is discharged to the container P in the rinse chamber 61, through the introduction pipe 57, the gas retention chamber 56 and the gas supply nozzle 48. The air to be continuously supplied acts on the inner circumferential surface and outer circumferential surface of the container P, and prevents the humid ozone gas G2 from remaining in the container P.

The rinse chamber 61 is provided with the exhaust pipe 65, and the gas in the interior of the rinse chamber 61 is emitted to the exterior through the exhaust pipe 65.

The container P having passed through the rinse area 60 is transferred to the third rotating table 43, and is carried to the downstream process.

[Effects]

Effects to be exerted by the above-described sterilization system 1 will be described.

The sterilization system 1 uses the humid ozone gas G2 as the sterilization component.

Ozone does not produce resistant bacteria, and does not remain in the container P even in the case where the container P is composed of PET. Further, it is unnecessary to provide treatment equipment that is necessary in the case of using a liquid agent.

Figure 7:
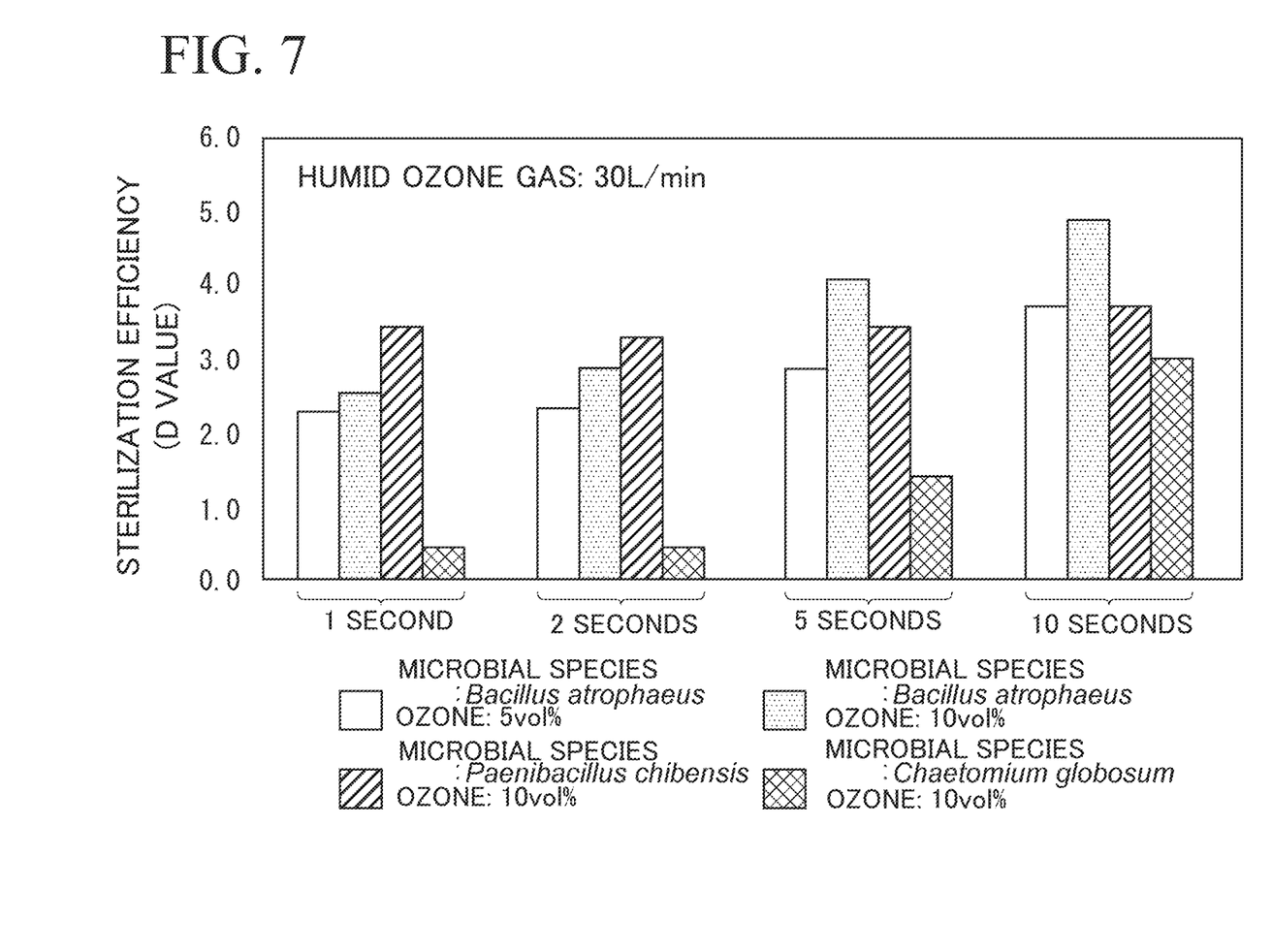
FIG. 7 is a graph showing a result of a sterilization efficiency evaluation performed using the humid ozone gas.

Moreover, by using the humid ozone gas G2, the sterilization system 1 can sufficiently obtain a sterilization efficiency required for the beverage container P. That is, the inventors performed a sterilization efficiency evaluation using the humid ozone gas G2, and as a result, as shown in FIG. 7, a sufficient sterilization power D value was obtained as the sterilization efficiency for the container. The D value is defined as follows.

$$D \text{ value} = \log[I/(MV)]$$

I: Initial bacteria count, MV: Viable bacteria count after sterilization treatment Further, the sterilization system 1 controls the operation of the humid gas generation unit 10, such that the optimal relative humidity RH at the temperature of the container P to be conveyed to the sterilization area 50 is obtained, and therefore, can sufficiently bring out the sterilization efficiency of the humidity ozone gas G2. Moreover, the temperature of the sterilization chamber 51 is controlled such that the humid ozone gas G2 acts preferentially on the container P, and therefore, the humid ozone gas G2 to be supplied can be used for the sterilization of the container P, without being needlessly consumed. Furthermore, in the sterilization area 50, the restriction of the height of the sterilization chamber 51 is provided in accordance with the elevation corresponding to the operation of the transfer of the container P. Therefore, it is possible to suppress the amount of the humid ozone gas G2 necessary for the sterilization, and therefore, it is possible to suppress the increase in the cost required for the sterilization.

Further, by providing the shield cylinder 47 in the sterilization region 53, the sterilization system 1 can concentrate the supplied humid ozone gas G2 inside the shield cylinder 47, and therefore, can efficiently perform the sterilization of the container P.

In the above, the preferred embodiment of the present invention has been described. Without departing from the spirit of the present invention, the constituents mentioned in the above embodiment can be selectively adopted, or can be appropriately modified to other constituents. In the following, some modifications will be described.

[Humidification Method]

In the sterilization system 1, the bubbling method, which is a type of bubble dissolution method, is used for generating the humid ozone gas G2. However, in the present invention, the method for generating the humid ozone gas G2 may be an arbitrary method.

For example, an ejector method, which is known as another method of the bubble dissolution method, can be employed.

Further, a mixing method of mixing an ozone gas and a humid gas such as a humid oxygen that are separately generated, a shower method of supplying an ozone gas to the water dispersed as a shower, and the like can be employed.

Further, the humid ozone gas G2 can be generated by generating ozone water by an arbitrary method and thereafter vaporizing the ozone water, or by generating a water vapor by an arbitrary method and making an ozone gas contact with the water vapor.

[Relative Humidity Control]

The sterilization system 1 measures the temperature of the container P, and regulates the humidity of the humid ozone gas G2 to be generated by the humid gas generation unit 10, in accordance with the temperature of the container P. However, the method for controlling the relative humidity RH of the humid ozone gas G2 to be supplied to the container P is not limited to this. That is, the present invention can control the relative humidity RH of the humid ozone gas G2 to be supplied to the container P, also by regulating the temperature of the container P while keeping a constant humidity as the humidity of the humid ozone gas G2 to be generated by the humidification apparatus 30. In this case, the temperature of the container P to be supplied to the sterilization area 50 may be previously measured, and the container P may be cooled or heated such that a necessary relative humidity RH is obtained.

In an example of the application of the present invention in the beverage filling system, the system of the present invention is disposed, for example, in the downstream process of the molding apparatus for the container P, and the container P that has just been molded is sterilized. The molding of the container P involves the heating of the preform, and the molded container P has a temperature of about 70° C., for example. Depending on the temperature of the humid ozone gas G2 and the relative humidity RH, the container P needs to be cooled. Further, in another example of the application of the present invention in the beverage filling system, the container P that has already been molded and has been preserved is sterilized. In this case, the temperature of the container P is about a room temperature (for example, 25° C.). Depending on the temperature of the humid ozone gas G2 and the relative humidity RH, the container P needs to be heated. For the cooling or heating of the container P, cool air or hot air may be blown to the container P, for example.

[Suction Method]

Next, the humid ozone gas G2 is blown such that the humid ozone gas G2 acts on the container P in the sterilization area 50, but the present invention is not limited to this. That is, in the present invention, by depressurizing the interior of the container P, it is possible to make the humid ozone gas G2, which is supplied to the periphery of the container P, sucked into the interior of the container P, and to make the humid ozone gas G2 act on the inner circumferential surface and the outer circumferential surface. Hereinafter, this method will be abbreviated to the suction method. An example thereof will be described with reference to FIG. 4B and FIGS. 6A to 6F. In FIG. 4B and FIGS. 6A to 6F, the same reference numerals as those in FIG. 4A and FIGS. 5A to 5F are assigned to the same constituent elements as those shown in FIG. 4A and FIGS. 5A to 5F. In the following, differences from FIG. 4A and FIGS. 5A to 5F will be mainly described.

Figure 4B:
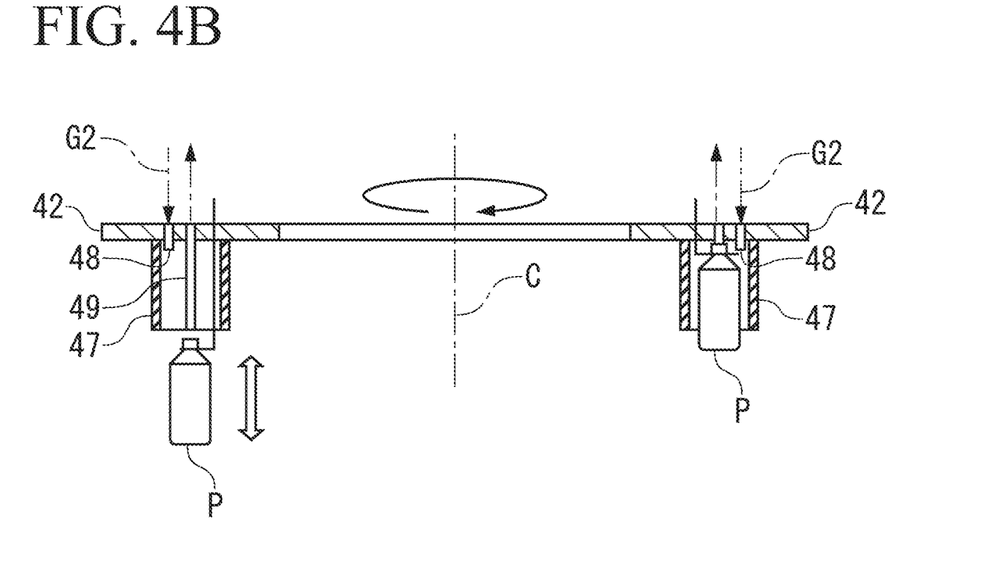

In the embodiment related to the suction method, a suction nozzle 49 for depressurizing the interior of the container P is provided, and the gas supply nozzle 48 for supplying the humid ozone gas G2 is provided. The suction nozzle 49 is connected with a vacuum pump, and the vacuum pump is actuated based on the instruction from the control unit 70. The gas supply nozzle 48 is connected with the second pipe 39 of the humidification apparatus 30, and the humid ozone gas G2 generated by the humidification apparatus 30 is supplied to the interior of the sterilization chamber 51, through the second pipe 39 and the gas supply nozzle 48. Here, the suction nozzle 49 is provided at a position that matches with the central axis of the container P when the container P is arranged at a predetermined sterilization position. Further, the gas supply nozzle 48 is provided, in planar view, inside the shield cylinder 47 and outside the container P when the container P is arranged at the predetermined position.

In the following, a sterilization procedure in the suction method for the container P will be described with reference to FIGS. 6A to 6F.

The container P continuously conveyed from the upstream side is transferred to the second rotating table 42 through the first rotating table 41. The second temperature sensor 58 measures the temperature of the container P transferred to the second rotating table 42, and the control unit 70 acquires the result. The processes up to here are the same as those in the blow method.

Figure 6A:
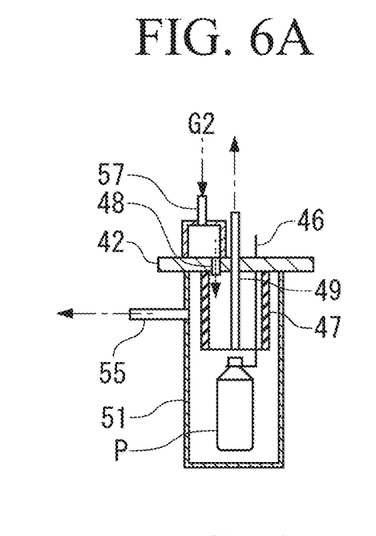
FIG. 6A to FIG. 6F are diagrams showing a procedure for sterilizing the container P in the suction mode.
Figure 6B:
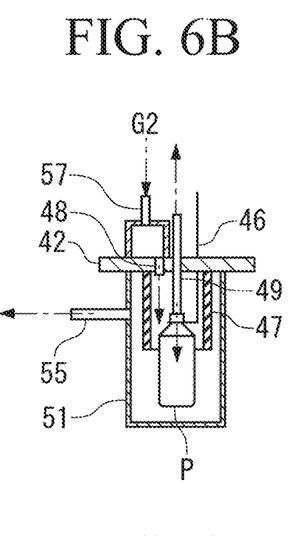
Figure 6C:
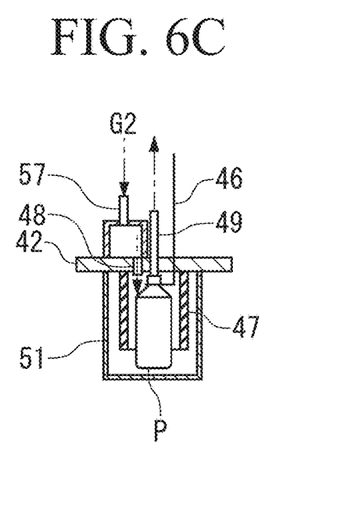
Figure 6D:
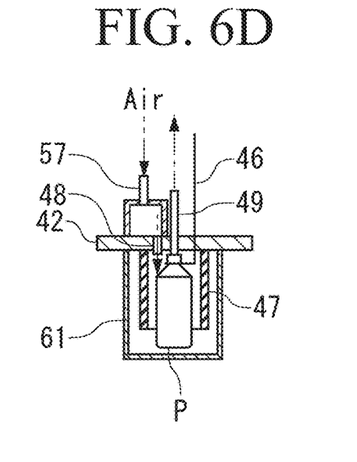
Figure 6E:
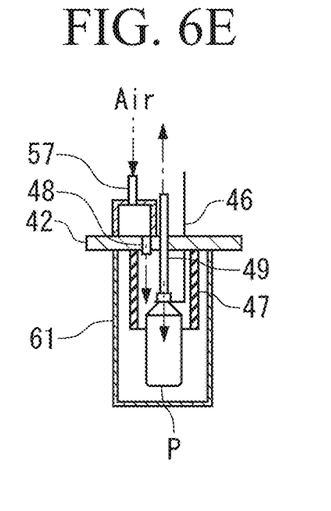
Figure 6F:
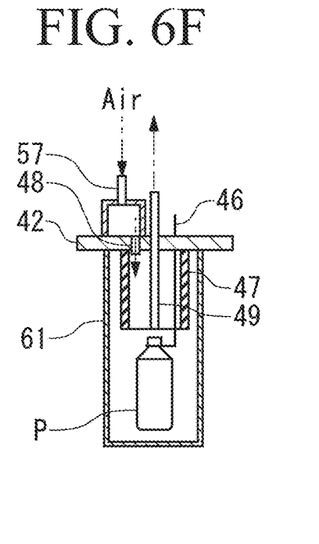

In the emission region 52, the interior of the container P is depressurized through the suction nozzle 49, and the humid ozone gas G2 is supplied to the interior of the shield cylinder 47 from the gas supply nozzle 48. The gas in the interior of the sterilization chamber 51 is emitted to the exterior through the exhaust pipe 55 (FIGS. 6A and 6B).

After passing through the emission region 52, the container P reaches the sterilization region 53.

In the sterilization region 53 (FIG. 6C), the humid ozone gas G2 is supplied to the periphery of the container P while the interior of the container P is depressurized. Therefore, after the contact with the outer circumferential surface of the container P, the humid ozone gas G2 is sucked into the interior of the container P, and further, is emitted to the exterior through the suction nozzle 49.

After passing through the sterilization region 53, the container P reaches the gas retention chamber 56. The subsequent processes are the same as those in the blow method, including the processes in the rinse area 60.

In the sterilization treatment by the suction method, the air in the interior of the container P is emitted in the emission region 52, and then, the container P is conveyed to the sterilization region 53. That is, the interior of the container P to be conveyed to the sterilization region 53, in which the air hardly remains, has already been filled with the humid ozone gas G2. Therefore, it is possible to make the humid ozone gas G2 efficiently act on the container P.

Other than the above, the constituents mentioned in the above embodiment can be selectively adopted, or can be appropriately modified to other constituents, without departing from the spirit of the present invention.

The invention claimed is:

1. A container sterilization method of performing sterilization by supplying a sterilization component to containers that are continuously conveyed along a predetermined conveyance path,
  the container sterilization method comprising supplying a humid ozone gas to a sterilization region, the humid ozone gas comprising an ozone gas that has humidity, the sterilization region being partitioned by a chamber that comprises the conveyance path, wherein
  the humidity of the humid ozone gas to be supplied to the sterilization region is regulated, depending on a temperature of the containers to be conveyed to the sterilization region.

2. The container sterilization method according to claim 1, wherein a humidity of the humid ozone gas to be supplied to the sterilization region is adjusted such that a relative humidity RH of the humidity ozone gas at the temperature of the containers to be conveyed to the sterilization region is in a range of 45 to 100%.

3. The container sterilization method according to claim 1, wherein the containers comprise PET (Polyethylene terephthalate).

4. The container sterilization method according to claim 1, wherein
  the humid ozone gas to be supplied to the sterilization region has a higher temperature than the containers to be conveyed to the sterilization region.

5. The container sterilization method according to claim 1, wherein the chamber has a higher temperature than the containers to be conveyed to the sterilization region.

\* \* \* \* \*